United States Patent
Abbondanza et al.

(10) Patent No.: US 9,474,935 B2
(45) Date of Patent: Oct. 25, 2016

(54) ALL-IN-ONE SMART CONSOLE FOR EXERCISE MACHINE

(71) Applicants: James M. Abbondanza, Lewiston, NY (US); Jackson Hsieh, City of Industry, CA (US)

(72) Inventors: James M. Abbondanza, Lewiston, NY (US); Jackson Hsieh, City of Industry, CA (US)

(73) Assignees: PROVA RESEARCH INC., Lewiston, NY (US); PARADIGM HEALTH & WELLNESS INC., City of Industry, CA (US)

( * ) Notice: Subject to any disclaimer, the term of this patent is extended or adjusted under 35 U.S.C. 154(b) by 0 days.

(21) Appl. No.: 14/515,540

(22) Filed: Oct. 16, 2014

(65) Prior Publication Data

US 2015/0111698 A1    Apr. 23, 2015

Related U.S. Application Data

(60) Provisional application No. 61/961,357, filed on Oct. 17, 2013.

(51) Int. Cl.
*A63B 24/00* (2006.01)
*G06F 19/00* (2011.01)
*A63B 22/00* (2006.01)
*A63B 22/02* (2006.01)
*A63B 22/06* (2006.01)

(52) U.S. Cl.
CPC ....... *A63B 24/0087* (2013.01); *G06F 19/3481* (2013.01); *A63B 22/0056* (2013.01); *A63B 22/0076* (2013.01); *A63B 22/02* (2013.01); *A63B 22/0605* (2013.01); *A63B 22/0664* (2013.01); *A63B 2225/20* (2013.01); *A63B 2225/50* (2013.01); *A63B 2230/062* (2013.01)

(58) Field of Classification Search
CPC .............. A63B 24/00; A63B 24/0062; A63B 24/0087; A63B 24/0064; A63B 71/0619; A63B 22/0056; A63B 22/0076; A63B 22/02; A63B 22/0605; A63B 22/0664; A63B 2225/20; A63B 2225/50; A63B 2230/062; G09F 19/3481
See application file for complete search history.

(56) References Cited

U.S. PATENT DOCUMENTS

| | | | | |
|---|---|---|---|---|
| 6,902,513 | B1* | 6/2005 | McClure | A63B 24/0006 482/4 |
| 7,938,752 | B1* | 5/2011 | Wang | A63B 24/0087 434/247 |
| 8,876,661 | B2* | 11/2014 | Lu | A63B 71/0619 482/1 |
| 9,028,370 | B2* | 5/2015 | Watterson | G06F 19/3481 482/1 |
| 2011/0090092 | A1* | 4/2011 | Birrell | G06Q 10/06 340/870.07 |
| 2013/0012357 | A1* | 1/2013 | Wang | A63B 24/00 482/4 |
| 2013/0225370 | A1* | 8/2013 | Flynt | G06F 19/3481 482/4 |

* cited by examiner

*Primary Examiner* — Glenn Richman
(74) *Attorney, Agent, or Firm* — Raymond Y. Chan; David and Raymond Patent Firm

(57) ABSTRACT

An all-in-one smart console, which is a self-contained unit, includes a control module for controlling an operation of the exercise machine, a command system operatively linked to the control module for receiving exercise related information from the exercise machine and data from the portable wireless communication device, and a fitness analysis module operatively linked to the control module for collecting exercise related information of the exercise machine and generating an exercise result based on the exercise related information.

16 Claims, 2 Drawing Sheets

ALL-IN-ONE SMART CONSOLE FOR EXERCISE MACHINE

CROSS REFERENCE OF RELATED APPLICATION

This is a non-provisional application that claims the benefit of priority under 35 U.S.C. §119 to a provisional application, application No. 61/961,537, filed Oct. 17, 2013.

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

1. Field of Invention

The present invention relates to an exercise machine, and more particularly to an all-in-one smart console equipped in an exercise machine, which simplifies the configuration among the console of the exercise machine, the portable wireless communication device, and the server, so as to enhance the mutual efficiency of each of the exercise machine, the portable wireless communication device, and the server, and to allow the all-in-one smart console to act as an autonomous machine control system, containing all of the communication, command, control, analysis and display hardware, firmware, and software, necessary to completely manage the training or exercise with the exercise machine.

2. Description of Related Arts

A conventional exercise machine, such as a treadmill, usually comprises a running platform and a control link provided in front of the running platform for allowing a user to communicatively link to a portable wireless communication device of the user, such as mobile phone or tablet, in order to control the operation of the running platform. Since different users will use the same exercise machine, the users are able to use their own portable wireless communication devices to wirelessly link to the exercise machine, such that exercise-related information can be transmitted from the exercise machine to the portable wireless communication device. The user is able to download a corresponding application in the portable wireless communication device to store and analyze the exercise-related information. Therefore, the user is able to create a personal profile to control the exercise machine. However, the storage space of the portable wireless communication device is limited so that the storage space of the portable wireless communication device will be eventually full when the exercise-related information is accumulatively saved in the portable wireless communication device. Furthermore, the microprocessor of the portable wireless communication device must be powerful enough to analyze the exercise-related information. In other words, the battery life of the portable wireless communication device will be shortened in order to execute the analysis of the exercise-related information.

Therefore, the conventional advanced exercising system further incorporates with a network server to directly store, update, and analyze the exercise-related information from the exercise machine, wherein the portable wireless communication device can only access the network server to view the exercise-related information therein. After analyzing the exercise-related information, the network server of the conventional system could be arranged to automatically program and control the exercise machine corresponding to the exercise-related information. For example, when the heart rate of the user is detected above a threshold calculated corresponding to the exercise-related information, the network server will send a deactivating signal to the exercise machine to turn off the exercise machine. Therefore, the network server will automatically control the exercise machine to prevent the user being over-exercising. However, it is dangerous to adjust the machine, such as the speed and the resistance of the machine, during the exercise or to stop the exercise machine suddenly when the user is exercising. In fact, the exercise machine should be only controlled by the user because only the user understands his or her own healthy habits and efforts.

SUMMARY OF THE PRESENT INVENTION

The invention is advantageous in that it provides an all-in-one smart console for an exercise machine, which simplifies the configuration among the exercise machine, the portable wireless communication device, and the server, so as to enhance the mutual efficiency of each of the exercise machine, the portable wireless communication device, and the server.

Another advantage of the invention is to provide an all-in-one smart console equipped in the exercise machine, which acts as an autonomous machine control system, containing all of the communication, command, control, analysis and display modules, firmware, and software, necessary to completely manage the training or exercise of a user on the exercise machine. In which, the system of the all-in-one smart console can be updated via IR, BT, WIFI, ANT, or the like in a wireless manner.

Another advantage of the invention is to provide an all-in-one smart console, which is able to function independently of the portable wireless communication device.

Another advantage of the invention is to provide an all-in-one smart console, which is the only one device to compute and analyze exercise related information from the exercise machine to generate an exercise result. Therefore, no software is required to install in the portable wireless communication device or in any alternative networked device to run the computation and analysis of the exercise related information.

Another advantage of the invention is to provide an all-in-one smart console, wherein no memory is required for the portable wireless communication device to store any exercise related information from the exercise machine or updated fitness information of the user.

Another advantage of the invention is to provide an all-in-one smart console, which is able to wirelessly connect to any external fitness equipment in order to collect the exercise related information from the external fitness equipment.

Another advantage of the invention is to provide an all-in-one smart console, which is adapted to incorporate with any existing exercise machine to provide a completely control of the exercise machine. Therefore, the present invention does not require to alter the original structural design of the exercise machine, so as to minimize the manufacturing cost of the exercise machine incorporating with the all-in-one smart console.

Another advantage of the invention is to provide an all-in-one smart console, wherein no expensive or complicated structure is required to employ in the present invention in order to achieve the above mentioned objects. Therefore, the present invention successfully provides an economic and efficient solution for integrating the exercise related information to the all-in-one smart console and for analyzing the exercise related information by the all-in-one smart console.

Additional advantages and features of the invention will become apparent from the description which follows, and may be realized by means of the instrumentalities and combinations particular point out in the appended claims.

According to the present invention, the foregoing and other objects and advantages are attained by a method for integrating exercise related information of a user from an exercise machine to a portable wireless communication device, comprising the following steps.

(A) Activate an all-in-one smart console to be communicatively linked to the portable wireless communication device.

(B) Control an operation of the exercise machine by the all-in-one smart console.

(C) During the user is exercising, collect exercise related information from the exercise machine by the all-in-one smart console.

(D) Generate an exercise result based on the exercise related information by the all-in-one smart console.

In accordance with another aspect of the invention, the present invention comprises an all-in-one smart console, which is a self-contained unit, comprising a control module for controlling an operation of the exercise machine, a command system operatively linked to the control module for receiving exercise related information from the exercise machine and data from the portable wireless communication device, and a fitness analysis module operatively linked to the control module for collecting exercise related information of the exercise machine and generating an exercise result based on the exercise related information.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

Figure 1:
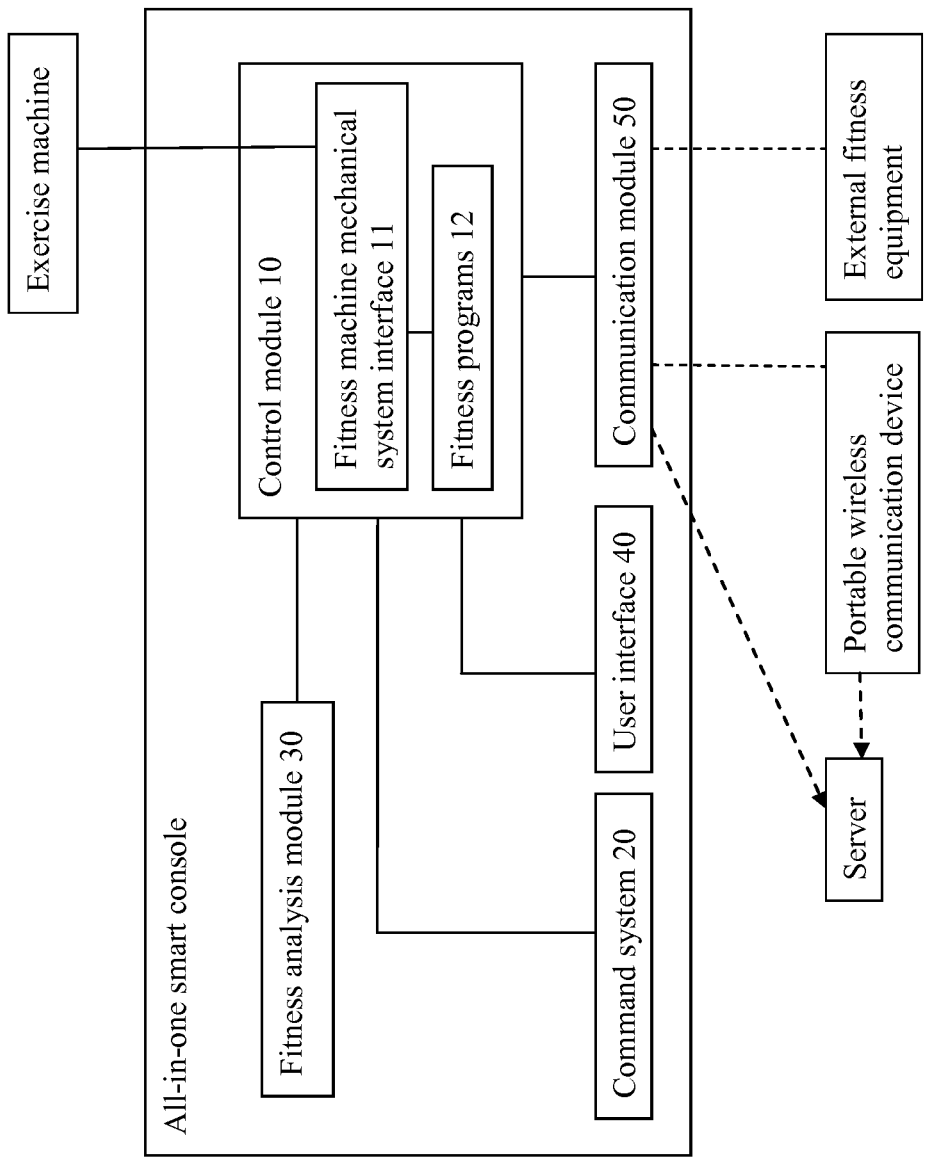
FIG. 1 is a block diagram of an all-in-one smart console according to a preferred embodiment of the present invention.

Referring to FIG. 1 of the drawings, an all-in-one smart console according to a preferred embodiment of the present invention is illustrated, wherein the all-in-one smart console is a self-contained unit to operatively link to an exercise machine and a portable wireless communication device. Accordingly, the exercise machine can be a treadmill, a stepper, an exercise cycle, an elliptical machine, or a rowing device or any other exercise or training device that requires data recording, analysis and any form of equipment motion reporting and/or control for the user to workout. The portable wireless communication device can be a mobile phone, a tablet, a PDA, or a computer.

According to the preferred embodiment, the all-in-one smart console comprises a control module 10 for controlling an operation of the exercise machine, and a command system 20 operatively linked to the control module 10 for receiving exercise related information from the exercise machine and data from the portable wireless communication device of the user. The all-in-one smart console further comprises a fitness analysis module 30 operatively linked to the control module for collecting exercise related information of the exercise machine and generating an exercise result based on the exercise related information.

The control module 10, which is a microprocessor-based master control to control the operation of the exercise machine. The control module 10 comprises a fitness machine mechanical system interface 11 to control different components of the exercise machine, such as servo, magnetic resistance, belt and lift motors. In particular, the fitness machine mechanical system interface 11 will communicates required commands to the exercise machine, and monitor and feed back the condition and/or state of the exercise machine that are receiving and executing the commands. These commands are determined by the component type of exercise machine with the commands including, but not limited to, lift up, lift down, speed up, speed down, increase or decrease mechanical tension. As a result, the portable wireless communication device cannot control the operation of the exercise machine.

Figure 2:
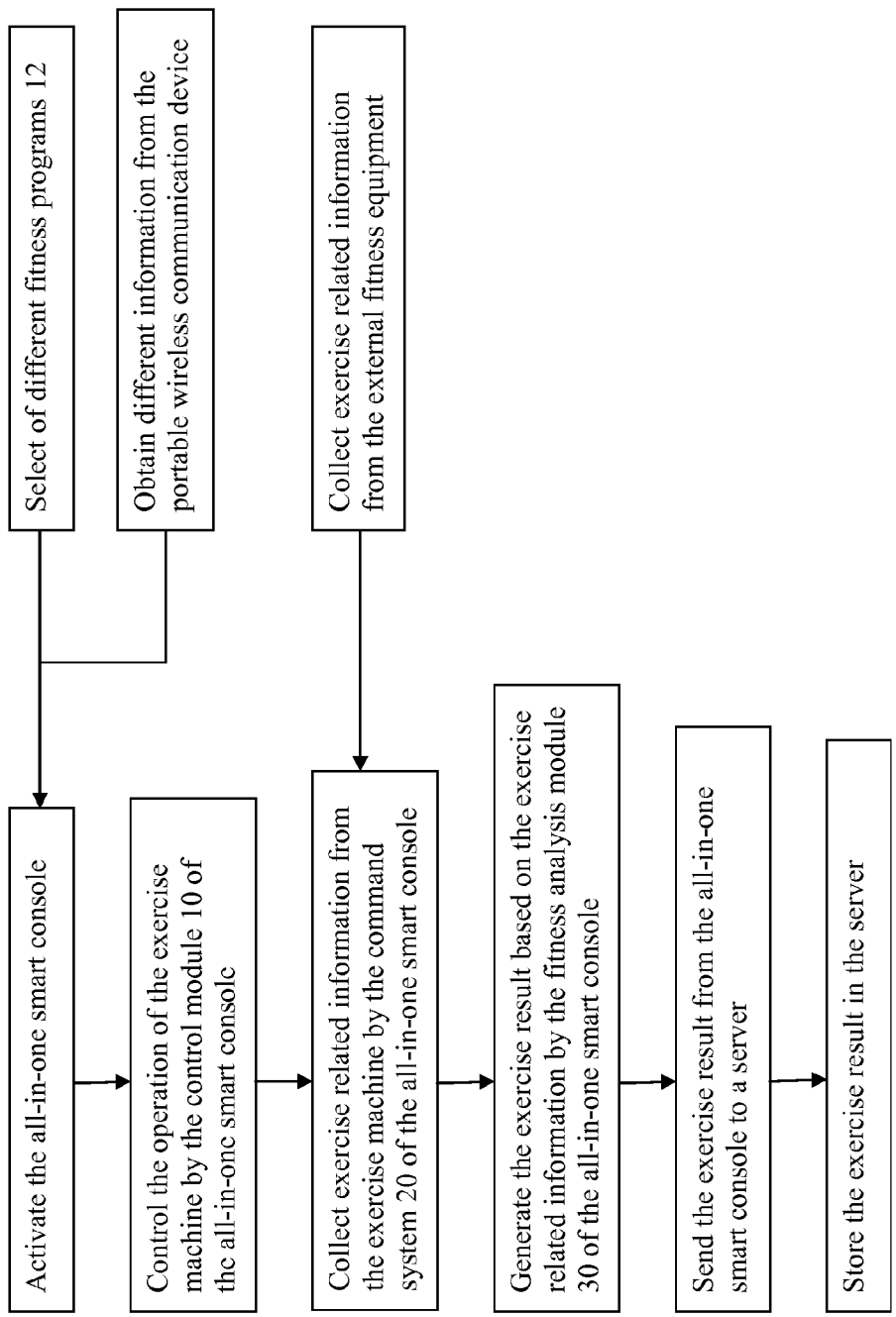
FIG. 2 is a flow diagram illustrating a method for integrating exercise related information of a user from an exercise machine to a portable wireless communication device through the all-in-one smart console according to the above preferred embodiment of the present invention.

In order to integrate the exercise related information of the user from the exercise machine to the portable wireless communication device, the present invention further provides an integration method, as shown in FIG. 2, which comprises the following steps.

(1) Activate the all-in-one smart console to be communicatively linked to the portable wireless communication device.

(2) Control the operation of the exercise machine by the control module 10 of the all-in-one smart console.

(3) During the user is exercising, collect exercise related information from the exercise machine by the command system 20 of the all-in-one smart console.

(4) Generate the exercise result based on the exercise related information by the fitness analysis module 30 of the all-in-one smart console.

(5) Send the exercise result from the all-in-one smart console to a server in such a manner that the portable wireless communication device is able to view the exercise result in the server. Or, alternatively, send the exercise result from the all-in-one smart console to a server via the portable wireless communication device which acts as a transmission device for data transmission.

(6) Store the exercise result of the user in the server as stored data for enabling the user to view only. Update the user's exercise data in the all-in-one smart console with the stored data in the server through the Internet or the portable wireless communication device which simply functions as means for transmitting data.

According to the preferred embodiment, the all-in-one smart console further comprises a user interface 40 controlled by the control module 10 for communicating with the portable wireless communication device that the portable wireless communication device serves as a remote display and input device only for the control module 10. When the control module 10 is activated in the step (1), the user interface 40 will automatically search for the portable wireless communication device. Once the portable wireless communication device is connected, preferably wirelessly connected, to the user interface 40, the user interface 40 will use the portable wireless communication device as a means for inputting and/or transmitting data to obtain user personal information, user biometric information, training options information, and/or data transmission information from the portable wireless communication device.

It is worth mentioning that the all-in-on smart console can also provide its built-in or remote input and display system, such as a monitor, touch screen, touch pad, key board, and etc., in the exercise machine for the user to input these information and interact directly with the all-in-one smart console. It is also a foreseeing alternative mode to pre-set the information in the portable wireless communication device by the user as a pre-configuration setting, such that once the connection between the user interface 40 and the portable wireless communication device is established, these information would be automatically received by the control module 10 through the user interface 40. Therefore, the portable wireless communication device will still serve as the input device of the control module 10 of the all-in-one smart console.

For example, an information program/application can be pre-installed into the portable wireless communication device to save the information. The user personal information contains screen name, first and last name of the user, address information, gender, birthday, user email address, and/or password. The user biometric information contains height, weight, displayed unit of measure, and/or activity level. The training options information contains exercise time, distance, and/or calories. The data transmission information contains information of the control module 10 and the server to be linked to the control module 10. The wireless connection between the control module 10 and the portable wireless communication device can be in form of "Bluetooth", "A.N.T.", "Infra-Red, "WiFi", or any other wireless data transfer technology. It should be appreciated that the portable wireless communication device can be connected to the control module 10 by cable.

According to the preferred embodiment, the portable wireless communication device will not process any health parameter corresponding to the user's disease state or condition, or user's health, nutrition, fitness or exercise state or condition to control the all-in-one smart console. In other words, the portable wireless communication device does not contain any personal digital assistant with wireless connectivity running the information application for accepting inputs of health parameter corresponding to the user's disease state or condition, or to the user's health, nutrition, fitness or exercise state or condition.

In the step (1), according to the preferred embodiment, once the control module 10 of the all-in-one smart console is activated to link with the portable wireless communication device, the portable wireless communication device serves as a remote display and input device only, so as to restrict the exercise related information to be exchanged between the all-in-one smart console and the portable wireless communication device. For example, for the treadmill or the elliptical machine, the exercise related information of the all-in-one smart console, such as the exercise level, elapsed time, calories, speed (MPH), distance (MILE), and pulse (BPM), will be displayed on the screen of the portable wireless communication device. Therefore, the user is able to view the exercise related information during exercising. In addition, as mentioned above, the all-in-one smart console is provided with its built-in or remote input and viewing system, so that when the user does not carry a portable wireless communication device during exercise, the user may still access the exercise related information through the screen of the input and display system of the all-in-one smart console.

Accordingly, the user interface 40 will also transmit the display data to the portable wireless communication device to display the status of the control module 10. For example, digital video and/or audio will be transmitted to the portable wireless communication device to show the status of the control module 10. Therefore, the portable wireless communication device not only serves as the input device but also serves as a display device of the control module 10 of the all-in-one smart console. Similarly, the user may also select to access such digital video and/or audio display data through the built-in input and display system of the all-in-one smart console of the exercise machine.

The control module 10 further comprises a plurality of different fitness programs 12 to be selected via the portable wireless communication device. In response to different fitness levels of the user, the user is able to select one of the fitness programs 12 in the control module 10 by the built-in input and display system of the all-in-one smart console of the exercise machine or the portable wireless communication device functioning as the input device. Once the fitness program is selected, the operation of the exercise machine will only be controlled by the control module 10 in the step (2). For example, a plurality of activation controls, such as "pause" and "stop" controls, are provided at the all-in-one smart console, such that the user is able to actuate the activation controls to control the operation of the exercise machine. Preferably, the screen of the all-in-one smart console can be a touch screen, wherein the activation controls are provided on the screen for the user to control by means of a touch.

According to the step (3), the command system 20 will collect the exercise related information from the exercise machine during the user is exercising. It is worth mentioning that the exercise machine will only be controlled by the control module 10 while the user is exercising, such that there is no control of the exercise machine by the portable wireless communication device. In other words, the portable wireless communication device is preferred to merely function as the input device for the user to input information and make selection of programs and functions of all-in-one smart console remotely and the display device for the user to access information from the all-in-one console of the exercise machine. Furthermore, the portable wireless communication device has no need to store the exercise related information from the exercise machine. Therefore, no memory is required in the portable wireless communication device to store such exercise related information. All the exercise related information is preferred to be collected by the all-in-one smart console.

It is worth mentioning that the portable wireless communication device does not provide any exercised related information by itself or receive data indicating a physiologic status of the user directly from the user, especially while the user is exercising.

The all-in-one smart console is able to communicate with an external fitness equipment, such as a heart rate transmitter worn by the user. In particular, the all-in-one smart console further comprises a communication module 50 operatively linked to the control module 10 for wirelessly connecting with the external fitness equipment so as to collect the exercise related information from the external fitness equipment to the command system 20. For example, the communication module 50 can wirelessly link to the heart rate transmitter, such that a user heart rate will only be collected by the all-in-one smart console via the heart rate transmitter worn by the user in order to generate the exercise result. It is worth mentioning that the user heart signal will not be transmitted to the portable wireless communication device in order to control the all-in-one smart console of the exercise machine by the portable wireless communication device. In other words, the portable wireless communication device will only function as a remote display of the all-in-one smart console, but will not effect or control any changes in the exercise parameters of the user, will not send any information to the external fitness equipment, and will not store or update any exercise related information from the external fitness equipment, such that the exercise related information from the external fitness equipment will not be stored in or analyzed by the portable wireless communication device. In addition, the exercise related information from the external fitness equipment will not be stored in the memory of the external fitness equipment. The wireless connection between the communication module 50 and the fitness equipment can be in form of "Bluetooth", Radio frequency (RF), Infrared (IR), or "WiFi". It is worth mentioning that the connection between the control module 10 and the portable wireless communication device is formed via the communication module 50.

It is worth mentioning that, during the exercise, fitness information and exercise information corresponding to the exercise will only be updated directly to the fitness analysis module 30 of the all-in-one smart console. In other words, during the exercise, no fitness information will be updated to the fitness analysis module 30 and no exercise information corresponding to the exercise will be sent to the exercise machine through the portable wireless communication device for changing the exercise machine setting or predetermined routine fitness information. Therefore, the portable wireless communication device has no need to contain any exercise communication module that can send a subset of updated fitness information during the user workout.

Once the workout is completed, all the exercise related information from the exercise machine will be automatically collected. The exercise related information will then be analyzed by the fitness analysis module 30 to generate the exercise result. In other words, the calculation and analysis of the exercise related information will be performed by the fitness analysis module 30 of the all-in-one smart console but not by the portable wireless communication device. Accordingly, the exercise result may will measure the strength and weakness of the user with fitness assessments. Therefore, the exercise result may will show the before and after workout and/or compare the current exercise result with the previous exercise result(s) to measure the improvement of the physical fitness of the user. It is worth mentioning that the all-in-one smart console is prohibited to communicate with the server until the exercise result generated by the all-in-one smart console has been sent to the server, such that no exercise related information will be sent to the server during the user is exercising.

The exercise result will be sent to the server, such as a "cloud server" for the user to view. The server and the all-in-one smart console will combined to form an exercise system for integrating exercise related information of the user from the exercise machine to the portable wireless communication device. Accordingly, once the workout is completed, a notification will be generated by the control module 10 to notify the generation of the exercise result. The notification will be sent to the portable wireless communication device to inform the user that the exercise result has been created by the fitness analysis module 30. Therefore, the user is able to actuate the all-in-one smart console, such as press a send button on the all-in-one smart console, or actuate the portable wireless communication device, such as touch a send button on the portable wireless communication device, in order to transmit the exercise result to the server. It is worth mentioning that since the data transmission information contains information of the server, the exercise result will send to the designated server, such as an Internet site, corresponding to the data transmission information. Preferably, the exercise result will be transmitted via the data protocol of the portable wireless communication device to the server if available. Alternatively, the exercise result can be transmitted by a way of a "WiFi-enabled" network to which the portable wireless communication device is presently connected. It should be appreciated that the exercise result can be transmitted through any network directly established between the all-in-one smart console and the server. According to the preferred embodiment, the exercise related information from the exercise machine will not be sent to the server for analysis and computation and will be analyzed and computed in the all-in-one smart console for such exercise result. In one embodiment, the server will not receive any information corresponding to the health parameter of the user from the portable wireless communication device and the exercise result computed in the all-in-one smart console is transmitted to the server from the all-in-one smart console through the Internet. In another embodiment, the portable wireless communication device can be functioned as a transmitting device while the all-in-one smart console has no internet connection with the server, wherein the exercise result computed in the all-in-one smart console is transmitted to the server via the portable wireless communication device. For example, the all-in-one smart console transmits the exercise result to the portable wireless communication device through Bluetooth or IR, and the portable wireless communication device can transmit such exercise result computed by the all-in-one smart console to the server through its Internet connection with the server.

Once the exercise result is stored in the server, the user is able to access the server at any time and any place to view the exercise result. According to the preferred embodiment, the server will not compare the personal data and/or the exercise result with other different users. In other words, the user can only view his or her own exercise result(s). However, a user may request access of another user's exercise result and information upon approval of the other user, for example though a charting or communication APP.

It is worth mentioning that the all-in-one smart console of the present invention will enhance the efficiency of each of the exercise machines, the portable wireless communication device, and the server, wherein each of them will effectively get its own job done individually. In other words, the all-in-one smart console will only obtain the exercise related information of the exercise machine in a real time manner to collect the information of before and after workout, such that the portable wireless communication device will not require collecting the exercise related information from the exercise machine in a real time manner. During exercising, the exercise related information will be? transitionally send to the all-in-one smart console. Therefore, the portable wireless communication device will not require large storage space to store the exercise related information. Furthermore, the user is able to carry his or her own portable wireless communication device and link to different exercise machines in any sequent order. For example, the user may first link his or her portable wireless communication device to the all-in-one smart console of a bicycle machine and exercise for a certain period of time while his or her exercise result computed by the all-in-one smart console of the bicycle machine will be stored in the server. Then, the user may link his or her portable wireless communication device to a treadmill machine and exercise for another certain period of time and his or her exercise result computed by the all-in-one smart console of the treadmill machine will also be stored in the server. Therefore, the user may also use his or her portable wireless communication device linked to server through Internet to access his or her exercise result stored in the server.

The all-in-one smart console will receive the exercise related information from the exercise machine. Then, the all-in-one smart console will send the exercise result analyzed by the all-in-one smart console to the server after exercising. Therefore, the portable wireless communication device will not require powerful calculating power to analyze the exercise related information. It is worth mentioning that multiple users can access the all-in-one smart console of any exercise machine by disconnecting one of the portable wireless communication devices from the all-in-one smart console and connecting the all-in-one smart console with another portable wireless communication device. In other words, the all-in-one smart console is activated to connect one portable wireless communication device at one time.

It is appreciated that the all-in-one smart console can be a computer, a dedicated internet site, or Google Chromecast type device to be connected to the exercise machine by the user for total portability to exercise in front of any television with full graphical display and remote input, which is embodied as the portable wireless communication device.

It is appreciated that the all-in-one smart console of the present invention can be alternatively a dedicated tablet computer wired directly to the exercise machine for data transmission and power, able to communicate with wireless communication devices, provide multiple user exercise programs, communicate directly with biological signal transmitters such as heart rate monitors, analyze those signals along with other user and machine supplied information to control exercise machine motors, lift and resistance systems and provide exercise related information in audio/visual form to the user.

It is appreciated that the all-in-one smart console of the preferred embodiment can be modified as a remotely located device communicating with the fitness machine and/or user via an APP on any smart mobile devices, smart televisions and other processing systems capable of communicating directly with the fitness machine and/or user.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A method for integrating exercise related information of a user from an exercise machine to a portable wireless communication device, comprising the steps of:
   (a) activating an all-in-one smart console to be communicatively linked to said portable wireless communication device;
   (b) controlling an operation of said exercise machine by said all-in-one smart console;
   (c) during exercise, collecting exercise related information from said exercise machine by said all-in-one smart console;
   (d) generating an exercise result based on said exercise related information by said all-in-one smart console; and
   (e) sending said exercise result from said all-in-one smart console to a server that said portable wireless communication device is able to view said exercise result in said server.

2. The method as recited in claim 1 wherein, in the step (e), said all-in-one smart console is prohibited to communicate with said server until said exercise result generated by said all-in-one smart console is sent to said server.

3. The method, as recited in claim 1, further comprising a step (f) of storing said exercise result in said server for enabling the user to access and view.

4. The method, as recited in claim 2, further comprising a step (f) of storing said exercise result in said server for enabling the user to access and view.

5. A method for integrating exercise related information of a user from an exercise machine to a portable wireless communication device, comprising the steps of:
   (a) activating an all-in-one smart console to be communicatively linked to said portable wireless communication device;
   (b) controlling an operation of said exercise machine by said all-in-one smart console;
   (c) during exercise, collecting exercise related information from said exercise machine by said all-in-one smart console; and
   (d) generating an exercise result based on said exercise related information by said all-in-one smart console, wherein, in the step (a), said all-in-one smart console is activated that said portable wireless communication device serves as a remote display and input device only, so as to restrict said exercise related information to be exchanged between said all-in-one smart console and said portable wireless communication device.

6. The method as recited in claim 4 wherein, in the step (a), said all-in-one smart console is activated that said portable wireless communication device serves as a remote display and input device only, so as to restrict said exercise related information to be exchanged between said all-in-one smart console and said portable wireless communication device.

7. The method, as recited in claim 6, wherein said portable wireless communication device does not store said exercise related information from said exercise machine.

8. The method, as recited in claim 7, wherein the step (c) further comprises a step of collecting a user heart rate only by said all-in-one smart console via a heart rate transmitter worn by said user in order to generate said exercise result.

9. The method as recited in claim 8 wherein, in the step (b), said operation of said exercise machine is only controlled by said all-in-one smart console during exercise.

10. The method, as recited in claim 9, wherein the step (a) further comprises a step of providing a plurality of different fitness programs by said all-in-one smart console to be selected via said portable wireless communication device.

11. An exercise system for integrating exercise related information of a user from an exercise machine to a portable wireless communication device, comprising:

an all-in-one smart console, which is a self-contained unit, comprising a control module for controlling an operation of said exercise machine, a command system operatively linked to said control module for receiving exercise related information from said exercise machine and data from said portable wireless communication device, and a fitness analysis module operatively linked to said control module for collecting exercise related information of said exercise machine and generating an exercise result based on said exercise related information; and a server communicatively linked to said control module, wherein only said exercise result is sent to and stored in said server upon completion of the exercise.

12. The exercise system, as recited in claim 11, wherein said all-in-one smart console further comprises a user interface controlled by said control module for communicating with said portable wireless communication device that said portable wireless communication device serves as a remote display and input device only for said control module.

13. The exercise system, as recited in claim 11, wherein said all-in-one smart console further comprises a communication module operatively linked to said control module for wirelessly connecting with an external fitness equipment so as to collect said exercise related information from said external fitness equipment to said command system.

14. The exercise system, as recited in claim 11, wherein said all-in-one smart console is prohibited to communicate with said server until said exercise result generated by said all-in-one smart console is sent to said server.

15. The exercise system, as recited in claim 11, wherein said control module further comprises a plurality of different fitness programs to be selected.

16. The exercise system, as recited in claim 15, wherein said plurality of different fitness programs are selected via said portable wireless communication device functioning as an input device.

* * * * *